United States Patent [19]
Dawe

[11] Patent Number: 4,519,792
[45] Date of Patent: May 28, 1985

[54] INFUSION PUMP SYSTEM

[75] Inventor: Garfield A. Dawe, Lindenhurst, Ill.

[73] Assignee: Abbott Laboratories, North Chicago, Ill.

[21] Appl. No.: 447,377

[22] Filed: Dec. 6, 1982

[51] Int. Cl.³ ............................................. A61M 5/00
[52] U.S. Cl. .......................... 604/152; 128/DIG. 12; 137/528; 251/65; 417/413; 604/123
[58] Field of Search ................ 604/122, 123, 151–153, 604/65–67; 137/528; 251/65, 141; 417/413, 474–478; 128/DIG. 12

[56]      References Cited
U.S. PATENT DOCUMENTS

| 2,646,071 | 7/1953 | Wagner | 137/528 |
|---|---|---|---|
| 3,559,644 | 2/1971 | Stoft et al. | 604/123 |
| 3,605,741 | 9/1971 | Spencer | 604/246 |
| 3,890,968 | 6/1975 | Pierce et al. | 604/65 |
| 4,038,981 | 8/1977 | Le Fevre et al. | 604/65 |
| 4,142,524 | 3/1979 | Jassawalla et al. | 604/123 |
| 4,230,244 | 10/1980 | Zissimopoulos | 251/65 X |
| 4,437,815 | 3/1984 | McMullen | 604/152 X |

FOREIGN PATENT DOCUMENTS

862953  9/1981  U.S.S.R. ................................ 604/67

Primary Examiner—Dalton L. Truluck
Attorney, Agent, or Firm—Alan R. Thiele; Martin L. Katz

[57]      ABSTRACT

An infusion pump system is described containing a valved cassette which is used as a pumping chamber for conducting fluid from an upstream portion to a downstream portion of the system. The removable cassette contains magnetically biased valves at both ends. Externally mounted magnets bias the valves within the cassette to provide an opening of the inlet valve and closing of the output valve during the fill cycle and closing of the inlet valve and opening of the outlet valve during the pump cycle. Free flow of infusion fluid is allowed when the valved cassette is removed from the pump mounting member which houses the actuating magnets and the reciprocating actuator for the pumping chamber.

58 Claims, 11 Drawing Figures

INFUSION PUMP SYSTEM

BACKGROUND OF THE INVENTION

This invention relates to a pumping device for administering intravenous and intra-arterial liquids. More particularly, this invention relates to a pumping device which includes a valved pumping chamber wherein the inlet and outlet valves are magnetically operable.

The use of an infusion therapy system as a method of treating patients is well known in the prior art. These systems provide health care personnel with the means to administer medication, provide nutrition, prevent dehydration or assure infusion of necessary fluids into the body of a patient. Sterility in infusion therapy is presently maintained by using disposable devices which are sterilized before use and discarded after use thus eliminating the need for expensive, complex, and often uncertain resterilization. The rising cost of health care is a matter of substantial concern to those in need of medical treatment. Any new development must therefore be conceived with simplicity and low cost in mind.

The dosage of medication administered by infusion therapy varies over a wide range of values spread over an even wider range of times. The prescribed dosage of medication per unit of time may be translated into a flow rate for an infusion pump system. Very low flow rates are often characterized by pulsatile spurts of liquid through the infusion delivery system into the patient. This pulsatile flow has disadvantages in that the lumen in the needle used during venpuncture may become closed in the intervals between the spurts of fluid. This closing is caused by blood flowing back into the infusion delivery system through the venipuncture. The ideal situation is therefore to provide a uniform continuous flow of medication into a patient at the lowest possible rate settings for the infusion system employed. This is particularly important with medication having a short half-life such as Oxytocin as sold by Abbott Laboratories. In these situations the infusion system must maintain an appropriate level of medication within the patient's body concurrently with the drop in potency of the medication.

An examination of the fluid mechanics of an infusion fluid delivery system indicates that the fluid pressure within a patient's blood stream works against the intravenous or intra-arterial infusion of fluid. The blood pressure of the patient also has a tendency to cause reflux of blood back into the needle as indicated earlier. If blood remains in the lumen it has a tendency to clot and thereby cause a blockage to the intravenous or intra-arterial infusion of fluid. Hence, the need arises to provide a device which will assure a regulated uniform and continuous one-way intravenous or intra-arterial infusion of fluid into the body of a patient which will overcome the blood pressure of the patient and at the same time assure continuous purging of the needle used for venipuncture. Such a device would also provide a uniform and constant one-way flow to assure a continuous supply of medication or fluid matched to the treatment needs of a patient no matter how small or how large those needs may be.

On the supply or upstream side, not all infusion administration systems are set up in exactly the same fashion. The head or weight of column of fluid acting on the pump is dependent on the size of the equipment being used, the location of the pump in relation to the fluid source and the work habits of the attending nurse or physician. These variables directly affect the upstream pressure perceived by the pump. On the patient or downstream side, the position of the patient with respect to the pump directly affects the downstream pressure perceived by the pump. It is therefore desired to provide an infusion pump system whose operation is only negligibly affected by a change in the supply side or upstream head acting on the pump or a change in the downstream pressure perceived by the pump. Finally, the infusion administration system must prevent the flow of air or gas into the patient. Various designs of electronic and mechanical means associated with infusion fluid delivery systems have attempted to overcome these problems. These various means have often been characterized by complexity of design, difficult use, high cost or the need for complex valving arrangements and actuating mechanisms. In addition, infusion delivery systems must be designed to be quickly operational in order to allow health care personel the greatest amount of time to administer to more important treatment needs of a particular patient.

Proper pump priming is another area of concern for health care personnel. Any pump used in an infusion fluid administration system should both be easy to prime and clearly able to show positive visual indication of having been primed. Additionally, it is desirable to give an indication to the user that all components are assembled correctly. The appearance of a signal, the positioning of components without the exertion of undue force and proper orientation of internal parts supplies the user with the confidence that the infusion administration system is properly set up for operation. Once properly positioned in the pump actuator, primed and operating, there is also a need to give a positive visual indication of operation. Infusion fluids are often clear and when flowing give no positive visual perception of movement. Many pumps used in infusion flow control systems found in the prior art have been hidden from view by operating means or flow controllers. It is therefore an advantage of this invention to provide a pump system whose operation at all but the very smallest flow rates can be visually verified by health care personnel.

It is also an advantage of this invention to provide a disposable pumping chamber for an infusion delivery system with integral valving that is easy to use, simple to manufacture with repeatability and reliability and is low in cost. A further advantage is the provision of an intravenous or intra-arterial delivery system which prevents the flow of air into the patient through a venipuncture site during administration of intravenous or intra-arterial fluid as well as when the source of infusion fluid is depleted.

It is yet another advantage of this invention to provide an infusion pump system which is chemically substantially inert, easily sterilized, nonbreakable, light weight and exceedingly compact. Additionally, an infusion pump system is provided which does not require the sealing properties of gaskets or O-rings for leakproof operation.

Recent developments have regulated flow control of infusion fluid by the use of electro-mechanical devices; specifically low volume pumps with appropriate valving to assure quick priming and air free flow of fluid. These pump systems utilize pumping chambers generically called "cassettes".

Typical of the developmental work done on cassette designs are U.S. Pat. Nos. 4,199,307 and 4,273,121, and patent application Ser. No. 164,434 filed June 30, 1980, now U.S. Pat. No. 4,456,009, by the same assignee as in this application. Flow control of the pumped fluid is afforded by valves that are actuated by various mechanical and electrical means. Typical of the patents disclosing various valving means in general are U.S. Pat. Nos. 4,126,132; 3,976,402; 3,298,320; 3,559,644; 3,620,650; 4,142,524 and application Ser. No. 278,546 filed June 29, 1981 by the same assignee as in this application. Magnetic valving in intravenous flow systems was disclosed in U.S. Pat. No. 3,890,968 for a gravity system. The positive on-off action of the valves in U.S. Pat. No. 3,890,968 generated the pulsatile flow which this invention specifically avoids.

SUMMARY OF THE INVENTION

The infusion pumping system disclosed herein utilizes a valved pumping chamber. To assure that air or gas is not pumped by the system, the outlet valve must be biased closed with the attendant need to defeat the bias on the outlet valve during priming. The utilization of magnetically biased valves with a pumping chamber enables a biased outlet valve to prevent the pumping of air when in operation and free flow priming or gravity operation when the valved pumping chamber is removed from the magnetic field. More specifically, the use of ferro-magnetic balls, resilient rubber valve seats and permanently mounted magnets within the pump housing provides a method for a highly reproducible bias. Two such ferro-magnetic ball valve assemblies may be used: one for the inlet and one for the outlet. An opening pressure of approximately 0.1 psi at the inlet port and a 5 to 7 psi bias at the outlet port has indicated a substantial degree of effectiveness. Once magnetically biased, the valves become fluid pressure actuated. Specifically, the inlet valve will not open until the pumping chamber internal pressure is less than the infusion fluid source head pressure, thus preventing backflow of fluid. Similarly, the outlet valve will not open until the pumping chamber pressure exceeds the downstream pressure caused by the blood pressure of the patient, system filters and flow devices. Backflow or reflux of blood into the needle will thereby be prevented. The elimination of backflow or reflux of blood into the needle prevents the closing of the lumen in the needle and the resulting disabling of the infusion administration system. Mechanically operated valving systems associated with pumping chambers in infusion delivery systems must compromise in this regard. The timing of mechanically operated valves must be carefully programmed either electrically or mechanically to produce the requisite operating differential pressure at the highest level of the broad range of intravenous or upstream and intra-arterial or downstream pressures. Higher pressures of pump output may cause a bolus of solution to flow through the venipuncture into the patient. Lower pressures of pump output may permit backflow of the blood of the patient into the lumen of the venipuncture needle. Consequently, whatever pressure for pump output is selected, it is easily defeated by near zero upstream pressure of an open infusion system on the low end and maximum downstream operating pressure on the high end. The use of magnets to bias the valves controlling fluid flow provides the user the distinct advantage of being able to selectively remove valve bias by cancelling the magnetic field or removing the magnetically biased valves from the influence of the controlling magnets. In this manner the disclosed system provides a second capability for gravity operation where a manually adjustable clamp can be used to vary the flow rate of medication into a patient.

BRIEF DESCRIPTION OF THE DRAWINGS

A better understanding of the infusion pump system will be accomplished by reference to the drawings wherein.

DESCRIPTION OF THE EMBODIMENTS

Figures 1, 2:
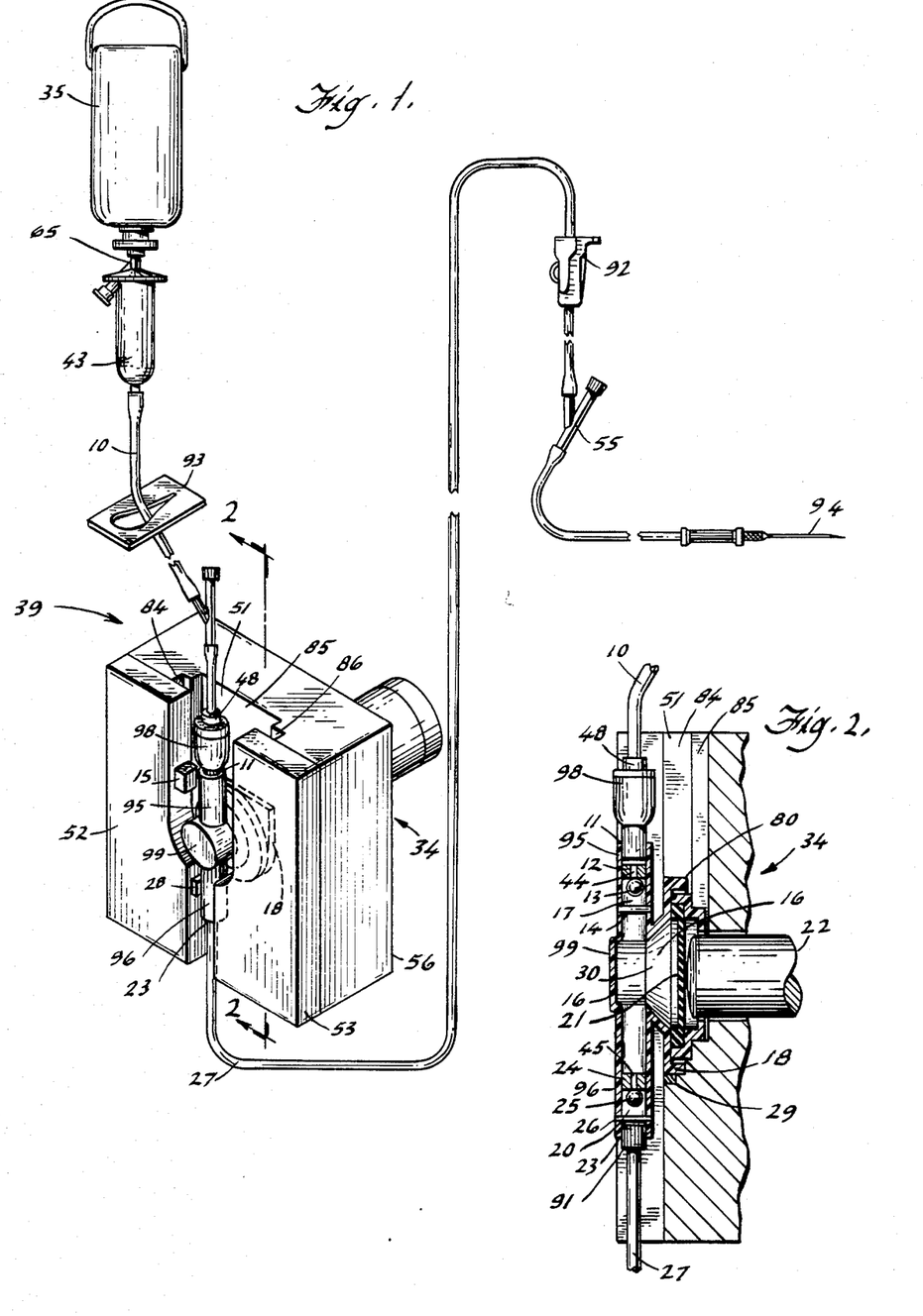
FIG. 1 is a perspective view illustrating the infusion pump system of this invention connected to a standard I.V. administration set which is shown in side elevation.
FIG. 2 is a view in vertical section taken along line 2—2 of FIG. 1 illustrating the mounting of the pumping chamber within the housing.

Proceeding to a detailed description of one embodiment of the present invention illustrated in FIGS. 1-5, the valved pumping chamber generally 99 is shown in FIG. 1 is used in an infusion pump system generally 39. As best seen in FIG. 1, the inlet port 11 of the valved pumping chamber 99 is mounted downstream from an air trap 98 and interconnected by upstream tubing 10 to a fluid source 35 through drip chamber 43. The outlet port 23 of the valved pumping chamber 99 is interconnected by downstream tubing 27 to suitable means for venipuncture such as a catheter or needle 94. The usual flow control tubing clamp 92 and Y-reseal site 55 are attached to tubing 27. FIG. 2 shows the valved pumping chamber 99 mounted in pump actuator generally 34, the magnetically permeable inlet flow restricting means or ball 13 is magnetically biased against inlet valve seat 12, thus making it a flow restricting means. Similarly, magnetically permeable outlet flow restricting means or ball 25 which similarly serves as a flow restricting means is magnetically biased against outlet valve seat 24. When removed from the pump actuator 34, the magnetically permeable balls 13 and 25 will fall away from valve seats 12 and 24, respectively, allowing an unobstructed path for free flow of fluid through inlet and outlet bores 44 and 45 respectively for gravity operation of the infusion system. Post members 14 and 26 extend transversely across the fluid passages containing balls 13 and 25 and valve seats 12 and 24. The post members 14 and 26 act as restraining means to prevent balls 13 and 25 from moving out of close proximity with respect to valve seats 12 and 24. These features are shown in more detail in FIGS. 3, 4 and 4a and will be later described.

Figures 6, 7, 8, 10:
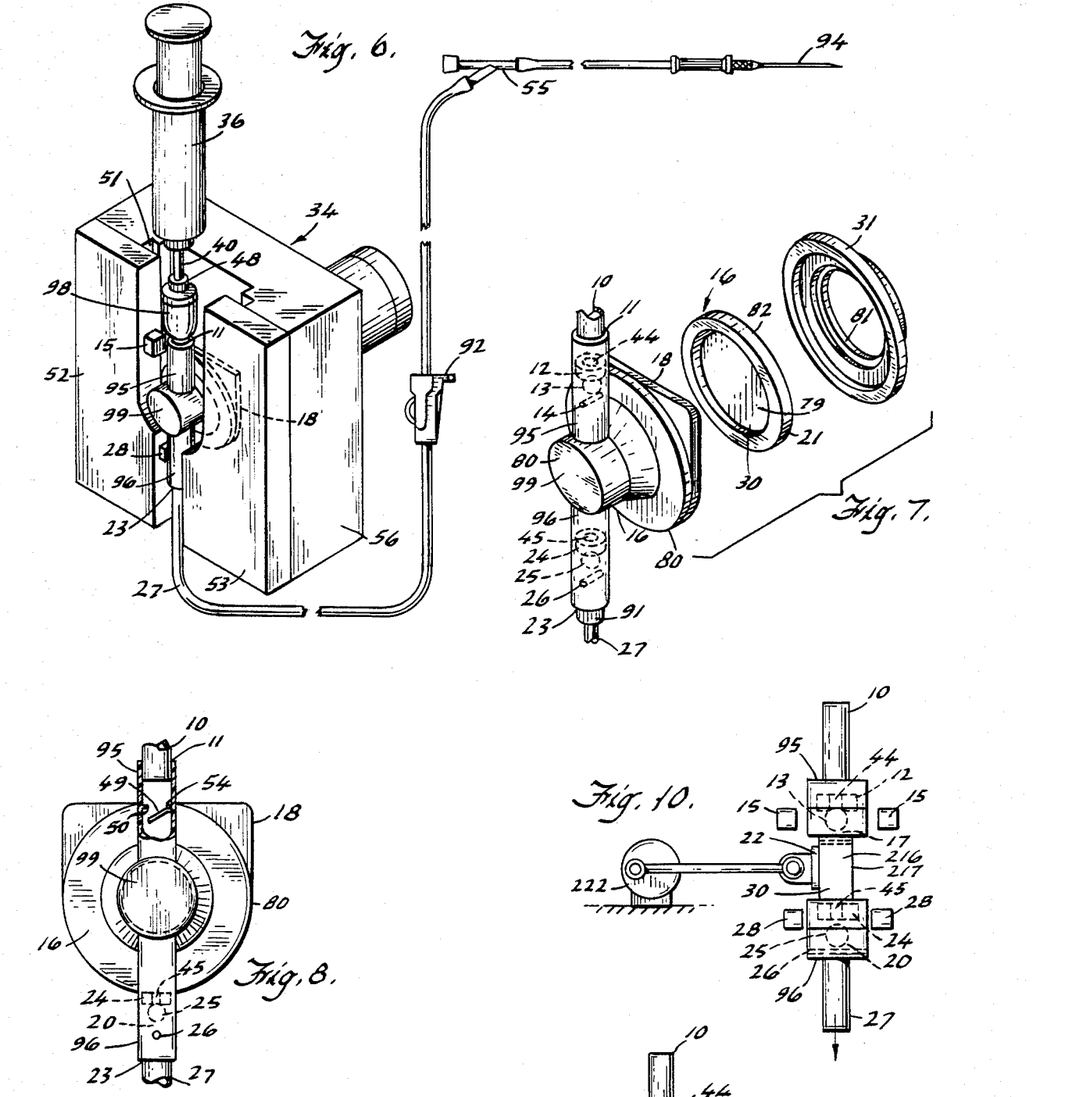
FIG. 6 is a perspective view of the infusion pump system similar to FIG. 1 illustrating the infusion pump system integrally connected to a syringe as the fluid source.
FIG. 7 is an exploded view of the valved pumping chamber utilized in the infusion pump system of FIG. 1.
FIG. 8 is a view in front elevation and with a portion broken away illustrating an alternate embodiment showing a flapper valve in the inlet port.
FIG. 10 is a view in side elevation of an infusion pump system using a section of tubing as a pumping chamber together with magnetically actuated inlet and outlet valves.

The mechanical means for retention of the valved pumping chamber 99 in pump actuator 34 is best seen in FIG. 1 and 2. In these figures, it will be seen that valved pumping chamber 99 and compartment 51 for accommodating the valved pumping chamber 99, are positioned so that they are transverse to the line of travel A—A of plunger member 22 with diaphragm 21 being centrally contacted thereby. This is afforded by step-like compartment 51 being composed of side slots 84 and 86 on either side of opening 85. Side slots 84 and 86 receive the oppositely extending outward portions of rigid wall 18 (FIG. 7). Opening 85 receives the diaphragmed portion of the valved cassette 99. Plunger member 22 moves transversely to the long axis of opening 85. In this manner mechanical mounting means are provided in the pump actuator 34 which have the same basic external configuration as the valved pumping chamber 99.

With reference to FIGS. 1 and 2 the cavity 30 within the pressure chamber 16 of valved pumping chamber 99 is interconnected to the upstream tubing 10 of the infusion delivery system 39 by inlet port 11 and interconnected to the downstream tubing 27 of the infusion delivery system 39 by outlet port 23.

The sectional view in FIG. 2 shows in more detail the valving arrangement of pumping chamber 99. Port 11 is in fluid connection with inlet valve assembly 95. Within inlet valve assembly 95 inlet valve seat 12 contains a bore 44, the opening and closing of which is accomplished by the action of ball 13 which affords a flow restricting means wherein ball 13 moves along a path 17, the limits of which are seat 12 and post member 14. When ball 13 rests against post member 14 an open path is provided whereas a closed flow path is afforded when ball 13 is biased against inlet valve seat 12. It will be noted that post member 14 is in the nature of a restraining means to maintain ball 13 in close proximity to valve seat 12. Pressure chamber 16 and diaphragm 21 provide a cavity 30 for the infusion fluid. Disposed at the opposite end of valved pumping chamber 99 is outlet valve assembly 96 with a valve seat 24 containing a bore 45 which is opened and closed in a manner similar to the bore 44 in inlet valve seat 12. This is accomplished by the action of ball 25 which affords a flow restricting means when moved along path 20, the limits of which are seat 24 and post member 26. The open position is described by ball 25 resting against post member 26 while the closed position biases ball 25 against valve seat 24. Extending beyond post member 26 is outlet port 23 which provides a connection for tubing 27. Disposed in pump actuator housing 56 is a limit switch 29 to signal proper seating of valved pumping chamber 99 in pump actuator 34.

Figure 3:
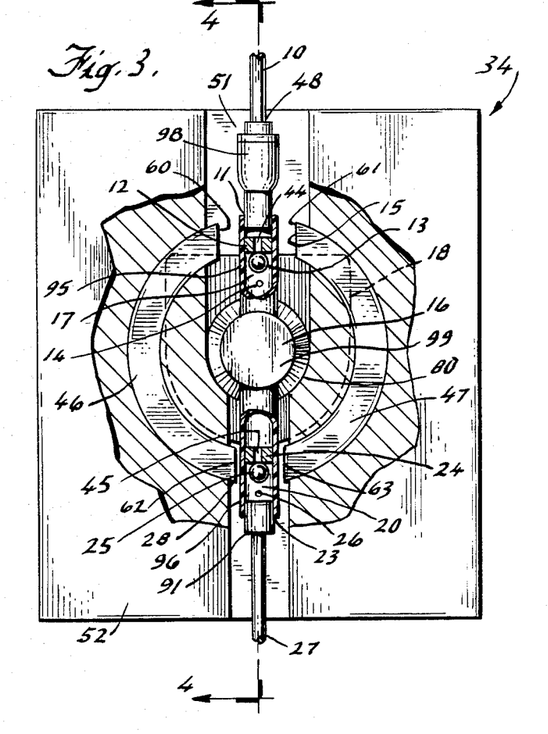
FIG. 3 is a view in front elevation of the infusion pump system of FIG. 1 with mounting covers for the magnetic means partially broken away removed to show placement of the valved pumping chamber with respect to the magnetic means.

Referring specifically to FIG. 3, the mounting covers 52, 53 of pump actuator 34 (FIG. 1) for magnets 46 and 47 have been partially removed to show the orientation of the magnets which provide a magnetic field 15 at the inlet valve assembly 95 and a magnetic field 28 at the outlet valve assembly 96 of the valved pumping chamber 99. In this instance, it will be noted that the ends 60 and 61 of the magnets 46 and 47, respectively adjacent ball 13 are spaced a greater distance apart than the ends 62 and 63 of the magnets 46 and 47 respectively adjacent ball 25. Accordingly, a greater magnetic effect will be produced on ball 25 in holding it against valve seat 24. Magnets 46 and 47 are set into slots (not shown) molded or machined in the covers 52 and 53 mounted on pump actuator housing 56.

Figure 4:
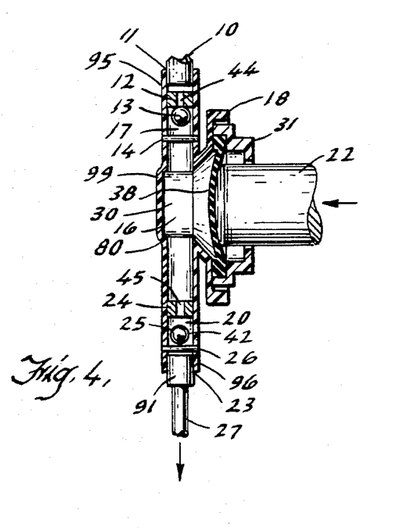
FIGS. 4 and 4a are side sectional views taken along line 4—4 of the infusion pump system shown in FIG. 3 showing in FIG. 4 the engagement of actuating means with the valved pumping chamber and the position of the valve means as the valved pumping chamber first empties and in FIG. 4a the filling of the pump chamber with fluid.
Figure 4A:
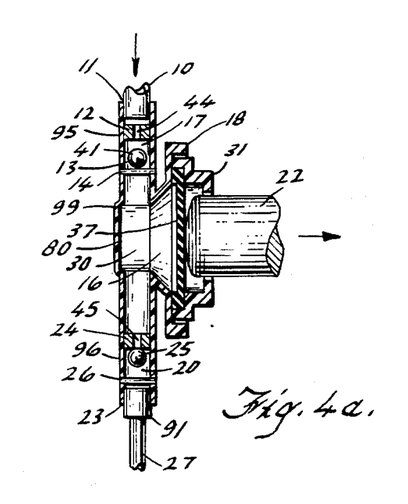

FIGS. 4 and 4a depict the relative location of balls 13 and 25 and plunger member 22 during pump operation. FIG. 4 depicts the cavity 30 within valved pumping chamber 99 at its smallest volume. This condition occurs as fluid is flowing from the cavity 30 through outlet valve assembly 96 into downstream tubing 27. FIG. 4a depicts the cavity 30 within valved pumping chamber 99 at its maximum volume. This condition occurs as fluid is flowing into the cavity 30 through inlet valve assembly 95 from upstream tubing 10. FIGS. 4 and 4a read together with FIG. 8 illustrate that rigid wall 18 and pump chamber portion 16 combine to form base member 80. Cavity 30 is described by pump chamber 16 and diaphragm 21. Rigid wall 18 provides the surfaces for locating and retaining the valved pumping chamber 99 in compartment 51 of pump actuator 34 (FIGS. 1, 3 and 6).

Figure 5:
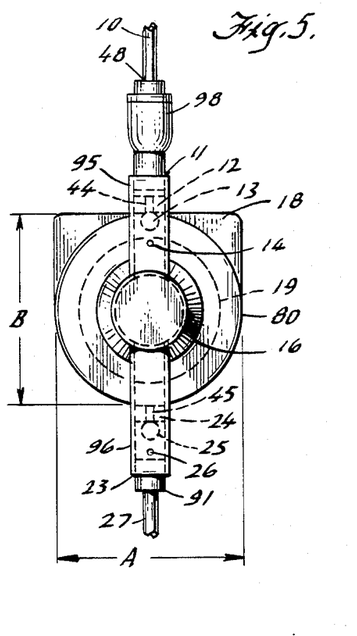
FIG. 5 is a front view in elevation of the valved pumping chamber shown in FIG. 1 illustrating the pumping chamber side.

Referring now to FIG. 5, it will be seen that inlet valve assembly 95 and outlet valve assembly 96 are mounted on and in fluid connection with pump chamber 16. Mounted on the opposing side is a retainer 31 which provides a flexible diaphragm 21 (FIG. 2), thus defining a cavity 30 (FIG. 2). Fluid enters the cavity 30 (FIG. 2) of the closed pressure chamber 16 by passing through inlet port 11 into inlet valve assembly 95, more specifically through the bore 44 of the inlet valve seat 12 past the inlet flow restricting means 13. Fluid leaves the cavity 30 (FIG. 2) of the closed pressure chamber 16 by passing through the outlet valve assembly 96, more specifically through the bore 45 of the outlet valve seat 34, past the outlet flow restricting means 25 and out through the outlet port 23.

FIG. 6 illustrates the embodiment of the invention wherein a syringe 36 is the source of fluid rather than container 35. The syringe 36 is connected directly or by fluid connecting means to air trap 98. This connection is effected by the frictional fitment of the nozzle portion 40 of the syringe 36 into an orifice 48 in air trap 98. The entire valved pumping chamber 99 is positioned within the pump actuator 34 as previously described in FIGS. 2 and 3 with the same reference numerals indicating the same parts.

As indicated in the exploded view of FIG. 7, closed pressure chamber 16 of valved pumping chamber 99 will be fabricated in three parts. To assemble the pumping chamber, diaphragm 21 will be placed between base member 80 and retainer 31. In this manner the outer portion 82 of diaphragm 21 will be frictionally engaged in an interior annular compartment of base member 80 and retainer 31. The flexible wall portion 79 of diaphragm 21 will be accessible through opening 81 in retainer 31. The base member 80 will be sealed to retaining member 31 by means of ultrasonic welding or a suitable adhesive. This results in a pumping cavity 30. The next step in the fabrication will be the placement of inlet valve assembly 95 and outlet valve assembly 96 in fluid communication with cavity 30 described within the combination of base member 80, diaphragm 21 and retainer 31. This combination of elements becomes valved pumping chamber 99. Upstream tubing 10 and downstream tubing 27 may be connected to ports 11 and 23 respectively. If required, an adapter 91 may be used to effect fluid-tight connections. It will be appreciated that the inlet and outlet tubing 10 and 27 will form a portion of an infusion pump system 39 with inlet tubing 10 being connected through an air trap such as 98 to a standard source of I.V. fluid 35 which includes a drip chamber 43. Outlet tubing 27 will be connected to a catheter or needle 94 as seen in FIG. 1.

FIG. 8 is another alternative embodiment showing a flapper valve 54 used in place of the magnetically permeable ball 13 and valve seat 12 composing inlet valve assembly 95 as seen in FIG. 2. The flapper valve 54 consists of a moving member 49 which is responsive to hydraulic pressure within closed pressure chamber 16. Fluid communication between upstream tubing 10 and closed pressure chamber 16 is prevented by seating of moving member 49 onto stop 50. The same reference characters have been employed to designate components having the same function, construction and relative location as in FIGS. 1–7.

Figure 9:
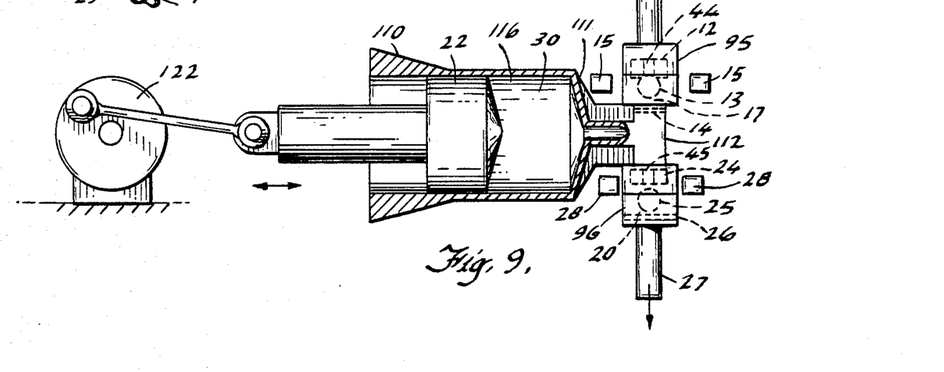
FIG. 9 is a view in side elevation and partially in vertical section of an infusion pump system using a syringe pumping chamber together with magnetically actuated inlet and outlet valves.

FIG. 9 is still another alternative embodiment showing a syringe mechanism 116 as the pumping chamber wherein the same reference numbers have been employed to designate components having the same function, construction and relative location as in FIGS. 1–7. Pressure chamber 116 is formed by syringe piston head 22 and nozzle end 111 of syringe body 110. Inlet valve assembly 95 is biased by magnetic means 15 and outlet valve assembly 96 is biased by magnetic means 28. The internal configuration of inlet valve assembly 95 and outlet valve assembly 96 is the same as illustrated in FIGS. 2, 4, 4a, 5 and 7. Rotating means 122 with eccentric movement transforms rotary motion into linear motion supplies reciprocating drive force to piston head 22.

FIG. 10 is yet another alternative embodiment showing a piece of flexible tubing 216 as the pumping chamber wherein the same reference characters have been employed to designate compounds having the same function, construction and relative location as in FIGS. 1–7. Pressure chamber 216 is formed within the inside diameter of tubing 217. Inlet valve assembly 95 is biased by magnetic means 15 and outlet valve assembly 96 is biased by magnetic means 28. The internal configuration of inlet valve assembly 95 and outlet valve assembly 96 is the same as illustrated in FIGS. 2, 4, 4a, 5 and 7. Rotating means 222 with eccentric movement transforms rotary motion into linear motion supplies reciprocating drive force to piston head 22.

OPERATION

A better understanding of the advantages of the infusion pump system 39 will be had by a description of its operation.

It is envisioned that sterile valved pumping chambers 99 with tubing attached will be contained in hermetically sealed packages which will be furnished to health care personnel. Operation of the infusion pump system 39 will be initiated by removing the valved pumping chamber 99 from its packaging together with upstream tubing 10 and downstream tubing 27 connected to the inlet port 11 and outlet port 23, respectively. The standard on/off slide clamp 93 is positioned to constrict upstream tubing 10. Flow control clamp 92 is positioned to prevent flow through downstream tubing 27. Fluid communication will be made with fluid container 35 by puncturing the sealing means of fluid container 35 (FIG. 1) with the vented piercing pin portion 65 of combined piercing pin and drip chamber member 43 to establish an appropriate indicator level in the drip chamber 43 (FIG. 1). Initial emptying of the fluid source 35 is prevented by the constricting of the upstream tubing 10 by the standard on/off, slotted clamp 93 (FIG. 1). To initiate priming of the system the entire valved pumping chamber 99 is held vertically in the inverted position with the outlet valve assembly on the top. Flow of fluid into the inverted valved pumping chamber 99 is initiated by releasing the upstream clamp 93 and flow control clamp 92. Flow of fluid is partially reduced by closing flow control clamp 92 when the fluid reaches flow control clamp 92. Without magnetic bias the magnetically permeable balls 13 and 25 will be moved into contact with inlet and outlet post members 14 and 26, respectively by the flow of fluid. Bores 44 and 45 in seats 12 and 24 respectively will be open and infusion fluid will flow through valved pumping chamber 99 and the remaining portions of the tubing by the influence of the head of fluid pressure caused by elevation of the fluid source 35. The inverting of valved pumping chamber 99 and release of the upstream clamp 93 and downstream clamp 92 will prime the infusion pump system 39 for operation. The downstream clamp 92 is then re-positioned on downstream tubing 27 to stop fluid flow in the infusion pump system 39 when all the air has been cleared from the system. The valved pumping chamber 99 is now mounted in pump actuator 34 by returning it to its upright position and sliding the primed valved pumping chamber 99 into compartment 51. Downstream tubing 27 is now attached to the venipuncture device 94. Proper seating of the valved pumping chamber 99 into compartment 51 of pump actuator 34 may be determined in two ways. First, limit switch 29 will close an electrical circuit which provides a signal that the valved pumping chamber 99 is properly in position for operation. Second, magnetically permeable balls 13 and 25 will appear to jump as the magnetomotive force of magnets 46 and 47 moves the magnetically permeable balls 13 and 25 from inlet and outlet post members 14 and 26 to inlet and outlet valve seats 12 and 24 respectively. Reciprocal operating means 22 is now activated to bring the internal pressure within cavity 30 to the pressure necessary to overcome the biasing force of outlet magnetic means 28. Upstream clamp 93 and downstream clamp 92 are positioned to allow fluid flow in tubing 10 and 27 respectively. During operation pump actuator 34 may be supported by a bedside table or other suitable structure. Controlled flow of fluid is obtained by the buildup and release of fluid pressure in the cavity 30 of closed pressure chamber 16.

The reciprocal operating means 22 as depicted in FIG. 4 may be connected to a stepper motor or any device which provides reciprocating linear motion. The reciprocal operating means 22 engages the diaphragm 21, moving it to position 38 (FIG. 4) so as to cause an increase of fluid pressure by a decrease in the volume of the cavity 30 of the closed pump chamber 16. This increase in fluid pressure acts on ball 13 along with the magnetomotive force of magnetic means 15 (FIG. 3). These two forces overcome the force of gravity as well as the viscosity of fluid on ball 13 and causes the ball 13 to press against inlet valve seat 12, thereby closing bore 44 and forming a fluid-tight seal preventing flow of fluid back into the fluid container 35 (FIG. 1) through tubing 10. In this manner there is only unilateral flow through inlet port 11 into cavity 30 of closed pressure chamber 16. The increase in fluid pressure within the cavity 30 of the closed pump chamber 16 is sufficient to overcome the magnetomotive force of magnetic means 28 (FIG. 3) causing the ball 25 to move away from the outlet valve seat 24 to a position as shown at 42 in travel path 20 (FIG. 4). Fluid will then pass through bore 45 of outlet valve seat 24 past ball 25 on through tubing 27 to the venipuncture site. Diaphragm 21 is permeable to gas but not to liquid. Therefore, as the pressure within cavity 30 of closed pump chamber 16 is increased, any air or gas trapped within cavity 30 is expelled into the atmosphere through the peripheral portion of diaphragm 21 that is not in contact with reciprocating means 22. In this manner inlet valve assembly 95 need only provide uni-directional flow of fluid, not bi-directional flow of both fluid and gas to effect purging of air or gas from the cavity 30. The axial movement of reciprocating means or plunger 22 along line A-A (FIG. 2) away from the valved pumping chamber 99 moves diaphragm 21 to a position as shown at 37 is depicted in FIG. 4a. Volume within the cavity 30 of the pressure chamber 16 is increased thereby causing a decrease in fluid pressure. Downstream from the cavity 30, magnetomotive force from magnetic means 28 (FIG. 3) causes the lower flow restricting ball 25 to move from restraining means 26 along travel path 20, closing bore 45 and forming a fluid-tight seal with outlet valve seat 24. The reduction in fluid pressure within cavity 30 of closed pressure chamber 16 also causes the force on ball 13 from within the closed pressure chamber 16 to be reduced.

The magnetomotive force of magnetic field 15 and the fluid pressure within cavity 30 is no longer sufficient to hold ball 13 against inlet seat 12 when placed under the influence of the weight of fluid from the fluid source 35 (FIG. 1) and the upstream tubing 10. This causes ball 13 to move from valve seat 12 to a position as shown at 41 along travel path 17 in inlet valve 95 (FIG. 4a). Fluid will now flow from the source 35 (FIG. 1) through tubing 10, air trap 98, and through the bore 44 in valve seat 12 past ball 13 into cavity 30 of closed pressure chamber 16.

Described above is the utilization of magnetically actuated balls with a flexible diaphragm type pumping chamber. Other types of pumping chambers may also be used with magnetically actuated flow restricting means. Shown in FIG. 9 is a syringe body 110 which forms a pressure chamber 116 in cooperation with the Tee-shaped fitting 112 attached to the nozzle end 111 of syringe body 110 and piston head or plunger 22. Plunger 22 is driven by linear drive means 122 which may also be a linear stepper motor. The valving action of magnetically permeable balls 13 and 25 against inlet and outlet valve seats 12 and 24 respectively is the same as with the diaphragm pump shown in FIGS. 4 and 4a. Shown in FIG. 10 is a piece of tubing 217 which forms a pressure chamber 216. Plunger 22 is driven by a linear drive means 222 which may also be a linear stepper motor. The valving action of magnetically permeable balls 13 and 25 against inlet and outlet valve seats 12 and 24 respectively is the same as with the diaphragm pump shown in FIGS. 4 and 4a.

An inherent feature of this invention is the gas disabling operation. It may best be explained by reference to FIGS. 2, 3, 4 and 4a. The magnetomotive force of magnetic means 15 is such that inlet flow restricting means 13 is urged into the closed position against valve seat 12 when there is no fluid in the infusion pump system 39. If air is drawn into the cavity 30, for example, when the reservoir 35 and drip chamber 43 are empty, the action of reciprocating means 22 against diaphragm 21 will only serve to compress the air in the space over the remaining incompressible fluid which now only partially fills cavity 30. The compression of the air within the cavity 30 of the pressure chamber 16 will be unable to create sufficient pressure within cavity 30 to overcome the magnetomotive force of magnetic means 28 holding outlet flow restricting means 25 on outlet valve seat 24. In this manner air will not be pumped into a patient through the venipuncture. The embodiments shown in FIGS. 9 and 10 will be similarly gas disabling. The ability of this invention to be converted to a gravity flow device may be best explained by reference to FIGS. 2, 3, 4 and 4a. Removal of the valved pumping chamber 99 from pump actuator 34 will cause balls 13 and 25 to drop from valve seats 12 and 24 along paths 17 and 20 to post members 14 and 26, respectively. This removal of the magnetic biasing of balls 13 and 25 against valve seats 12 and 24 allows an unrestricted path for flow of fluid through tubing 10, air trap 98, upper valve seat bore 44, cavity 30, lower valve seat bore 45 into lower tubing 27. While air trap 98 is not required for proper operation of valved pumping chamber 99 it provides a means to strip small bubbles from the intravenous fluid just upstream of inlet port 11. Any trapped bubbles of air or gas near the surface of the fluid will join the air space within air trap 98 rather than remaining with the fluid. Gas disabling of the infusion pump system 39 by the accumulation of air in cavity 30 is thereby prevented. In this regard the inherent gas disabling feature provides an extra measure of safety for the patient and reduces the frequency of flow-alarms. The embodiments shown in FIGS. 9 and 10 may be converted to gravity flow in the same manner as valved pumping chamber 99.

The base member 80 shown best in FIGS. 5 and 7 is composed of a clear styrene acrylonitrile plastic. However, it can be formed of a semi-rigid styrene acrylonitrile or other suitable plastic materials such as a clear polycarbonate. A clear acrylonitrile butadiene styrene could be used. Ideally, the retainer 31 (FIG. 7) will be made from the same material as base member 80. Diaphragm 21 is made of a gas permeable, hydrophobic silicon elastomer 70 Shore A. Other similar gas permeable, hydrophobic materials could be employed. Valve seats 12 and 24 are fabricated from a silicone rubber. Other suitable materials such as natural rubber or polyurethane may be used. Valve seats 12 and 14 may be shaped such as concave in configuration on the surface meeting the flow restricting balls 13 and 25 to increase the effectiveness of the fluid-tight seal. Balls 13 and 25 may be made from solid magnetically permeable stainless steel. Commercially available 5/32" O.D. balls have exhibited the desired characteristics to make the valve assemblies 95 and 96 operative. If desired, hollow stainless steel balls could be used or other suitable metals such as copper-nickel-chrome coated steel. Referring to FIG. 5, it has also been found that where dimension A of the valved pumping chamber 99 is approximately 1-9/16 inches and dimension B is approximately 1-9/16 inches, a chamber can be fabricated which is adequately fed by and easily connected to vinyl tubing with an approximate 0.100 inside diameter and an approximate 0.138 outside diameter. Should smaller tubing be used an adapter 91 may be placed on either inlet port 11 or outlet port 23. Satisfactory performance results have been achieved where the cavity 30 is sized to contain approximately 3.0 ml. of fluid. Control over movement of diaphragm 21 enables the user to control the volume of fluid pumped. This control may be achieved by proper timing and controlling the stroke length of operating means 22. A displacement volume of 0.5 ml. has proven to be effective in the prevention of gas disabling. Continued contact between operating means 22 and diaphragm 21 enhances accuracy. Programmed movement of operating means 22 is readily possible with commercially available and relatively inexpensive micro-computer chips. Functions such as flow rate, flow error, delivery volume or occlusion alarm may be easily handled by known digital techniques. It is preferable to design the controller for operating means 22 to provide return strokes of very short duration despite the length of the pumping stroke. In this manner, the flow of medicament into the patient will be nearly constant, interrupted only very briefly for the return stroke of operating means 22. Digital electronics capability makes such operation easily achievable. Upper and lower magnetic means 15 and 28 may be made from alnico permanent magnets or rare earth permanent magnets. Electromagnetic means may also be employed in place of permanent magnets. Pump actuator 34 houses the necessary electronic circuity and operating controls. In addition it provides a mounting for the reciprocating operating means 22. Covers 52 and 53 contain either machined or molded recesses to accommodate magnetic pieces 46 and 47. In addition, covers 52 and 53 form a pocket or U-shaped slot which cooperates with compartment 51 in pump actuator housing 56 to vertically and horizontally position the valved pumping chamber 99 with respect to reciprocal operating means 22 and magnetic means 15 and 28.

Performance testing of the described infusion pumping system has revealed that there is approximately a 0.9% change in flow rate when head heights are varied over the usual range found in health care facilities. Changing back pressure on the pump from 6 psi to −2 psi produces less than a 1% change in flow rate.

Additional testing has revealed that cycling the reciprocal plunger member approximately five times in quick fashion before the administration of liquid begins charges the entire system with adequate internal pressure to assure uniform flow of fluid during the following periods of fluid administration.

It will thus be seen that through the present invention there is provided a novel pumping system providing a regulated flow of fluids which is simple in its construction and easily used by health care personnel. The small number of components, the simplicity of component design and low component cost allow for ease of manufacture and disposal once used. In particular, the ports 11 and 23 can also be manufactured to serve as connecting means for the upper tubing 10 and lower tubing 27.

The foregoing invention can now be practiced by those skilled in the art. Such skilled persons will know that the invention is not necessarily restricted to the particular embodiments presented herein. The scope of the invention is to be defined by the terms of the following claims as given meaning by the preceding description.

I claim:

1. A valved pumping chamber for use in an infusion delivery pump system including first and second magnetic means and a pump actuating means including a reciprocal operating member, said pumping chamber operating between an upstream portion and a downstream portion of the infusion delivery system comprising:
    an inlet port;
    an inlet fluid passage means interconnecting with said pumping chamber;
    an inlet valve seat having a bore in said inlet fluid passage means;
    magnetically permeable flow restricting means constructed and arranged to be biased against said inlet valve seat under the magnetomotive force of said magnetic means;
    means for providing substantially constant and continuous magnetic force located outside of said inlet fluid passage means which maintain said magnetically permeable flow restricting means in proximity to said inlet valve seat;
    a pumping chamber defining a cavity and flexible means adapted to be engaged by said reciprocal operating member to change the internal volume of said pumping chamber;
    an outlet port;
    an outlet fluid passage means interconnecting with said pumping chamber;
    an outlet valve seat having a central bore disposed in said outlet fluid passage means;
    magnetically permeable flow restricting means constructed and arranged to be biased against said outlet valve seat under the magnetomotive force of said second magnetic means; and
    means for providing a substantially constant and continuous magnetic force located outside of said outlet fluid passage means which maintain said magnetically permeable flow restricting means in proximity to said outlet valve seat.

2. The valved pumping chamber as defined in claim 1 wherein said flexible means is defined by a flexible wall or diaphragm and said reciprocal operating member engages said diaphragm.

3. The valved pumping chamber as defined in claim 2 wherein said diaphragm comprises a substantially flat disc and is held in-part to said pumping chamber by frictional means.

4. The valved pumping chamber as defined in claim 1 wherein said flexible means is defined by a syringe piston head and said reciprocal operating member is operatively connected to said piston head.

5. The valved pumping chamber as defined in claim 1 wherein said flexible means is defined by a length of flexible, plastic tubing and said reciprocal operating member engages said tubing.

6. The valved pumping chamber as defined in claim 1 wherein said inlet port is positioned diametrically opposite from said outlet port.

7. The valved pumping chamber as defined in claim 1 wherein said inlet and outlet valve seats are constructed and arranged to provide fluid-tight seals in engagement with said flow restricting means.

8. The valved pumping chamber as defined in claim 1 wherein the upper and lower ports are adapted to receive flexible tubing.

9. The valved pumping chamber as defined in claim 1 wherein said magnetically permeable means are spherically shaped.

10. The valved pumping chamber as defined in claim 1 wherein said magnetically permeable means are defined by a magnetic ball members.

11. The valved pumping chamber as defined in claim 1 further including an air trap member operatively associated with said inlet port.

12. The valved pumping chamber as defined in claim 11 wherein said air trap member includes means to interconnect flexible tubing or a syringe device.

13. The valved pumping chamber as defined in claims 2 and 3 wherein said flexible diaphragm is composed of a hydrophobic material.

14. A valved pumping chamber for use in an infusion delivery pump including outlet magnetic means and a pump actuating means including a reciprocal operating member, said pumping chamber operating between an upstream portion and a downstream portion of the infusion delivery system comprising:
   an inlet port;
   an inlet fluid passage means interconnecting with said pumping chamber;
   a flapper valve disposed in said inlet fluid passage;
   a pumping chamber defining a cavity and flexible means adapted to be engaged by said reciprocal operating member to change the internal volume of said pumping chamber;
   an outlet port;
   an outlet fluid passage means interconnecting with said pumping chamber;
   an outlet valve seat having a central bore disposed in said outlet fluid passage means;
   magnetically permeable flow outlet restricting means constructed and arranged to be biased against said outlet valve seat under the magnetomotive force of said outlet magnetic means; and
   means for providing a substantially constant and continuous magnetic force located outside of said outlet fluid passage means which maintain said magnetically permeable flow restricting means in proximity to said outlet valve seat.

15. The valved pumping chamber as defined in claim 14 wherein said flexible means is defined by a flexible wall or diaphragm and said reciprocal operating member engages said diaphragm.

16. The valved pumping chamber as defined in claim 15 where said diaphragm comprises a substantially flat disc and is held in part to said pumping chamber by frictional means.

17. The valved pumping chamber as defined in claim 14 wherein said flexible means is defined by a syringe piston head and said reciprocal operating member is operatively connected to said piston head.

18. The valved pumping chamber as defined in claim 14 wherein said flexible means is defined by a length of flexible plastic tubing and said reciprocal operating member engages said tubing.

19. The valved pumping chamber as defined in claim 14 wherein said inlet port is positioned diametrically opposite from said outlet port.

20. The valved pumping chamber as defined in claim 14 wherein said inlet flapper valve and said outlet valve seat are constructed and arranged to provide fluid tight seals.

21. The valved pumping chamber as defined in claim 14 wherein the upper and lower ports are adapted to receive flexible tubing.

22. The valved pumping chamber as defined in claim 14 wherein said magnetically permeable outlet flow restricting means is spherically shaped.

23. The valved pumping chamber as defined in claim 14 wherein said magnetically permeable outlet flow restricting means is defined by a magnetic ball member.

24. The valved pumping chamber as defined in claim 14 further including an air trap member operatively associated with said inlet port.

25. The valved pumping chamber as defined in claim 14 wherein said air trap member includes means to interconnect flexible tubing or a syringe device.

26. The valved pumping chamber as defined in claims 15 and 16 wherein said flexible diaphragm is composed of a hydrophobic material.

27. An infusion pump of the diaphragm type comprising:
   a mounting member;
   first and second magnetic means;
   a plunger member; said first and second magnetic means and said plunger member operatively positioned in said mounting member with said plunger member therebetween;
   means constructed and arranged to move said plunger member in said mounting member in a reciprocal manner;
   a valved pumping chamber comprising:
   an inlet port;
   an inlet fluid passage means interconnecting with said pumping chamber;
   an inlet valve seat having a central bore in said inlet fluid passage means;
   magnetically permeable flow restricting means constructed and arranged to be biased against said inlet valve seat under the magnetomotive force of said first magnetic means;
   means for providing a substantially constant and continuous magnetic force located outside of said inlet fluid passage means which maintain said magnetically permeable flow restricting means in proximity to said inlet valve seat;
   a pump chamber defining a cavity and flexible means adapted to be engaged by said reciprocal plunger to change the internal volume of said pumping chamber;
   an outlet port;
   an outlet fluid passage means interconnecting with said pumping chamber;
   an outlet valve seat having a central bore disposed in said outlet fluid passage means;
   magnetically permeable flow restricting means constructed and arranged to be biased against said outlet valve seat under the magnetomotive force of said second magnetic means;
   means for providing a substantially constant and continuous magnetic force located outside of said outlet fluid passage means said magnetically permeable flow restricting means in proximity to said outlet valve seat;
   a compartment constructed and arranged in said mounting member to receive said pumping chamber and positioned to axially align said flexible diaphragm with the line of travel of the said plunger member;
   said first and second magnetic means positioned to bias said magnetically permeable flow restricting means against said inlet and outlet valve seats under the magnetomotive force of said first and second magnetic means.

28. The infusion pump as defined in claim 27 wherein said flexible means is defined by a flexible wall or diaphragm and said reciprocal operating member engages said diaphragm.

29. The infusion pump as defined in claim 28 wherein said diaphragm member comprises a substantially flat disc and is held in part to said pumping chamber by friction means.

30. The infusion pump as defined in claim 27 wherein said flexible means is defined by a syringe piston head and said reciprocal operating member is operatively connected to said piston head.

31. The infusion pump as defined in claim 27 wherein said flexible means is defined by a length of flexible, plastic tubing and said reciprocal operating member engages said tubing.

32. The infusion pump as defined in claim 27 wherein said inlet port is positioned diametrically opposite from said outlet port.

33. The infusion pump as defined in claim 27 wherein said inlet and outlet valve seats are constructed and arranged to provide fluid-tight seals in engagement with said flow restricting means.

34. The infusion pump as defined in claim 27 wherein the said upper and lower ports are adapted to receive flexible tubing.

35. The infusion pump as defined in claim 27 wherein said magnetically permeable means are spherically shaped.

36. The infusion pump as defined in claim 27 wherein said magnetically permeable means are defined by magnetic ball members.

37. The infusion pump as defined in claim 27 further including an air trap member operatively associated with said inlet port.

38. The infusion pump as defined in claim 27 wherein said air trap member includes means to interconnect flexible tubing or a syringe device.

39. The infusion pump as defined in claim 28 or 29 wherein said flexible diaphragm is composed of a hydrophobic material.

40. The infusion pump as defined in claim 27 including means responsive to the positioning of the valve chamber in said mounting member to generate an electrical signal.

41. The infusion pump as defined in claim 27 wherein said first and second magnetic means is defined by two permanent magnetic bar members with end portions positioned in spaced alignment.

42. The infusion pump as defined in claim 41 wherein said magnetic bar members have a curved configuration.

43. The infusion pump as defined in claim 27 wherein said second magnetic means is constructed to exert a greater magnetomotive force on said magnetic ball member operatively associated with said outlet valve seat than said first magnetic means exerts on said magnetic ball operatively associated with said inlet valve seat.

44. An infusion pump of the diaphragm type comprising:
   a mounting member;
   outlet magnetic means;
   a plunger member;
   said outlet magnetic means and said plunger member operatively positioned in said mounting member;
   means constructed and arranged to move said plunger member in said mounting member in a reciprocal manner;
   a valve pumping chamber comprising:
   an inlet port;
   an inlet fluid passage means interconnecting with said pumping chamber;
   a flapper valve disposed in said inlet fluid passage;
   a pump chamber defining a cavity and flexible means adapted to be engaged by said reciprocal plunger to change the internal volume of said pumping chamber;
   an outlet port;
   an outlet fluid passage means interconnecting with said pumping chamber;
   an outlet valve seat having a central bore disposed in said outlet fluid passage means;
   magnetically permeable flow restricting means constructed and arranged to be biased against said outlet valve seat under the magnetomotive force of said outlet magnetic means;
   means for providing a substantially constant and continuous magnetic force located outside of said outlet fluid passage means which maintain said magnetically permeable flow restricting means in proximity to said outlet valve seat; and
   a compartment constructed and arranged in said mounting member to receive said pumping chamber and positioned to axially align said flexible diaphragm with line of travel of the said plunger member;
   said outlet magnetic means positioned to bias said magnetically permeable flow restricting means against said outlet valve seat under the magnetomotive force of said outlet magnetic means.

45. The infusion pump as defined in claim 44 wherein said flexible means is defined by a flexible wall or diaphragm and said reciprocal operating member engages said diaphragm.

46. The infusion pump as defined in claim 45 wherein said diaphragm member comprises a substantially flat disc and is held in part to said pumping chamber by frictional means.

47. The infusion pump as defined in claim 44 wherein said flexible means is defined by a syringe piston head and said reciprocal operating member is operatively connected to said piston head.

48. The infusion pump as defined in claim 44 wherein said flexible means is defined by a length of flexible plastic tubing and said reciprocal operating member engages said tubing.

49. The infusion pump as defined in claim 44 wherein said inlet port is positioned diametrically opposite from said outlet port.

50. The infusion pump as defined in claim 44 wherein said inlet flapper valve and said outlet valve seat are constructed and arranged to provide fluid tight seals.

51. The infusion pump as defined in claim 44 wherein the said upper and lower ports are adapted to receive flexible tubing.

52. The infusion pump as defined in claim 44 wherein said magnetically permeable outlet flow restricting means is spherically shaped.

53. The infusion pump as defined in claim 44 wherein said magnetically permeable outlet flow restricting means defined by a magnetic ball member.

54. The infusion pump as defined in claim 44 further including an air trap member operatively asociated with said inlet port.

55. The infusion pump as defined in claim 44 wherein said air trap member includes means to interconnect flexible tubing or a syringe device.

56. The infusion pump as defined in claim 45 or 46 wherein said flexible diaphragm is composed of a hydrophobic material.

57. The infusion pump as defined in claim 44 including means responsive to the positioning of the valve chamber in said mounting member to generate an electrical signal.

58. The infusion pump as defined in claim 44 wherein said outlet magnetic means is defined by two permanent magnetic bar members with end portions positioned in spaced alignment.

* * * * *